(12) United States Patent
Bone Salat et al.

(10) Patent No.: US 9,861,443 B2
(45) Date of Patent: Jan. 9, 2018

(54) DEVICE FOR TREATING TRUNCAL AND/OR COLLATERAL VARICOSE VEINS AND A SYNERGISTIC PHYSIO-CHEMICAL METHOD FOR USE

(71) Applicants: Carlos Bone Salat, Costa d'en Blaines-Calvia (ES); Joaquina Fructuoso Gomez, Costa d'en Blaines-Calvia (ES)

(72) Inventors: Carlos Bone Salat, Costa d'en Blaines-Calvia (ES); Joaquina Fructuoso Gomez, Costa d'en Blaines-Calvia (ES)

(*) Notice: Subject to any disclaimer, the term of this patent is extended or adjusted under 35 U.S.C. 154(b) by 352 days.

(21) Appl. No.: 14/432,872

(22) PCT Filed: Oct. 21, 2013

(86) PCT No.: PCT/ES2013/070728
§ 371 (c)(1),
(2) Date: Apr. 1, 2015

(87) PCT Pub. No.: WO2015/059316
PCT Pub. Date: Apr. 30, 2015

(65) Prior Publication Data
US 2016/0346041 A1    Dec. 1, 2016

(51) Int. Cl.
*A61B 18/22* (2006.01)
*A61M 25/00* (2006.01)

(52) U.S. Cl.
CPC ......... *A61B 18/22* (2013.01); *A61M 25/0075* (2013.01)

(58) Field of Classification Search
CPC .......................... A61B 18/22; A61M 25/0075
See application file for complete search history.

(56) References Cited

U.S. PATENT DOCUMENTS

| 5,843,072 A | 12/1998 | Fururmoto et al. |
| 2007/0260229 A1 | 11/2007 | Navarro et al. |

FOREIGN PATENT DOCUMENTS

| ES | 2280692 T3 | 9/2007 |
| WO | 2010135793 A1 | 12/2010 |

OTHER PUBLICATIONS

International Search Report dated Jul. 7, 2014, corresponding to International Patent Application No. PCT/ES2013/070728.

*Primary Examiner* — Bradley Osinski
(74) *Attorney, Agent, or Firm* — Ladas & Parry LLP

(57) ABSTRACT

A device for treating truncal and/or collateral varicose veins, such that they may be treated fully at outpatient clinics, without the need to use local anesthetic, wherein the device links the energy or power flow emitted by the laser to the effect of the sclerosant foam and, using a method which links the physio-chemical properties of the two synergistically, removes the exceptional venous endothelium, in addition to reducing both the concentration of the sclerosant substance and that of the energy released by the laser into the vein/varicose vein, such that the entire method may be carried out fully at outpatient clinics and performed in the usual work area, without the need for a strict surgical environment or local anesthetic, with the exception of the same being used at the entry point, it not being necessary to administer local anesthetic in a perivenous, tumescent and/or truncal way.

8 Claims, 2 Drawing Sheets

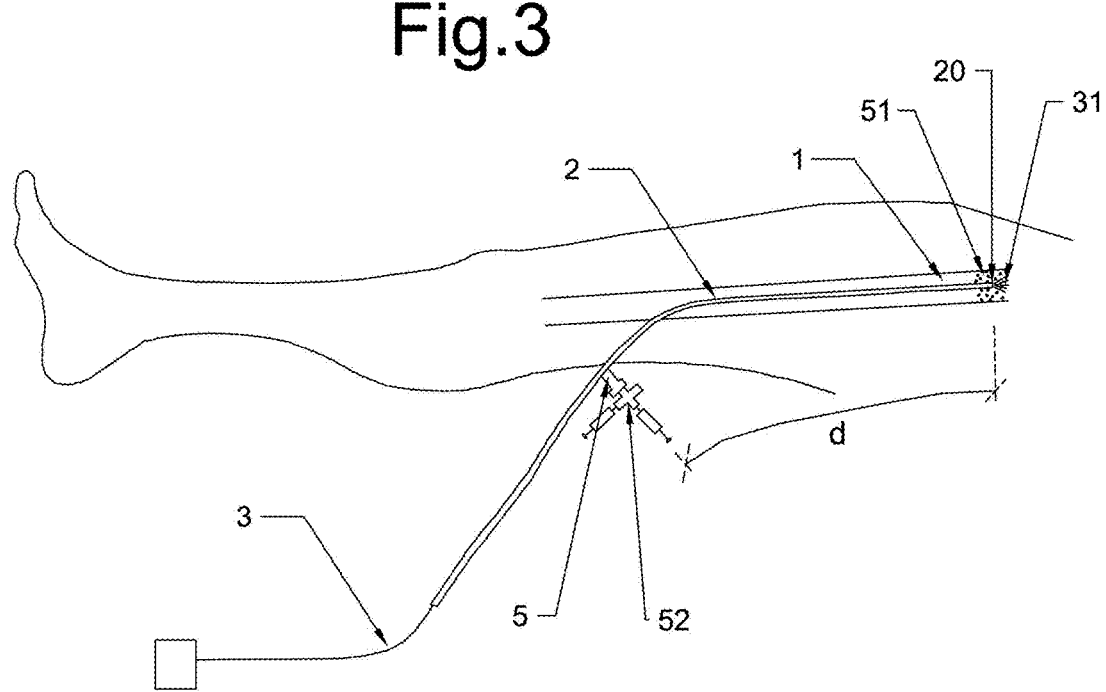

DEVICE FOR TREATING TRUNCAL AND/OR COLLATERAL VARICOSE VEINS AND A SYNERGISTIC PHYSIO-CHEMICAL METHOD FOR USE

This application is a 371 of PCT/ES2013/070728, filed on Oct. 21, 2013.

OBJECT OF THE INVENTION

A device for improving truncal varicose vein treatments at outpatient clinics, without the need for local anesthetic, be it perivenous, tumescent and/or truncal, in such a way that this device links the energy or power flow transmitted by the laser to the effects produced by the medication administered, through a technical method that synergistically links the physio-chemical properties of both together, in such a way that the exceptional venous endothelium may be removed, whilst also reducing both the energy released to the venous endothelium by the laser, and the concentration of the substance administered, considerably, thus meaning the entire process may be carried out at outpatient clinics alone, in traditional treatment rooms, without the need for a strict surgical environment.

BACKGROUND OF THE INVENTION

For over a decade, truncal varicose veins have most commonly been treated using minimally invasive techniques, such as endolasers, radiofrequency and echo guided sclerotherapy with microfoam drugs, thus leaving purely surgical techniques (stripping) for extremely developed cases.

These techniques continue to prevail, since they achieve the same or even better results than traditional treatments, and can be carried out at outpatient clinics. The Endovenous Laser Treatment (EVLT) method, also known as the endolaser technique, is currently one of the most commonly employed techniques, given that it is safe, effective and offers quick recovery. As is already known, it consists in introducing a thin optical laser fiber into the inside of the vein to be treated, thus removing and sealing off the damaged vein upon applying the energy needed and giving rise to subsequent healing.

Sclerosant medication is also injected intravenously in liquid form and/or as foam, in order to irritate the venous endothelium. The microfoam variety that contains less product furthermore produces a greater effect in terms of obliterating treated areas.

All other techniques, such as radiofrequency, the administration of water vapor at high temperatures and the application of sealant substances inside truncal varicose veins, seek the same outcome, i.e. to remove, seal and subsequently heal the vein and/or veins treated, in order to eliminate the condition.

Indeed, many registrations have been made within this field, which only use laser devices. Of these registrations, U.S. Pat. No. 6,398,777 by ENDOLASER ASSOCIATES LLC stands out, defining another, different device for treating varicose veins by emitting laser radiation through a fiber optic cable and an angiocatheter, the effect of which is produced through contact with the venous endothelium, but which is nevertheless different from the present invention in that it does not facilitate the administration of medication, since it requires much more energy. Indeed, the new invention reduces said energy by 90%. Moreover, the current patent facilitates or blocks contact with the inner wall of the vein, whilst the prior patent requires contact in all cases. Patent WO2006/052558 by COOLTOUCH INC, also stands out, since it develops a fiber optic device for treating varicose veins using an infrared laser, which defines an opening in the distal end thereof and defines a wave interval for correct usage. Patent US 2006/0189967 by MASOTTI LEONARDO also stands out, since it develops another device for treating varicose veins using laser radiation, specifically using a Holmium laser. Meanwhile, U.S. Pat. No. 5,053,033 by CLARKE stands out, since it also uses fiber optic technology, although the same is used to keep the blood vessel open and is of little use when it comes to treating varicose veins. Patent US2009/0264875 by WILLIAM M. APPLING stands out since it defines a laser device for treating varicose veins using an expandable separator located at its distal end, which enables the heat energy of the laser to be better distributed at said end. Meanwhile, U.S. Pat. No. 5,531,739 by TRELLES stands out, since it also uses a fiber optic probe to reach the underneath of the blood vessel to be treated, this methodology being completely different to that used as an object of the present invention. Patent US 2008071333 by HAYES CLINT stands out, since it develops another laser device with which to treat varicose vein conditions, by means of eliminating venous reflux in an underlying vein, introducing a catheter and emitting energy by means of a laser. Examples of registrations comprising a surgical method, such as patent EP311295 must also be highlighted, this patent making a piece of surgical apparatus comprising a waveguide of the fiber optic variety, for example, known, through which laser energy is applied. EP0152766 is furthermore noteworthy within the background art, since it reveals a piece of apparatus for reducing these problems by selectively using electromagnetic energy, whilst patent ES2132028 by Dr. CARLOS BONE—the same inventor as he who designed the present patent—must be highlighted, since it defines an endoluminal electro-coagulator for varicose vein operations, the same constituting a surgical instrument consisting of an electro-coagulating head-piece, joined to a flexible conductor wire. Likewise, patent ES2188398, also by Dr. CARLOS BONE, stands out, upon defining a piece of pocket laser apparatus, whilst patent WO2013081768 by VASCULAR SOLUTIONS is noteworthy, with an expandable, extendible device for the occlusion of varicose veins. Patent WO2010135793 by EDUARDO SISTEROLLI must be mentioned within the background literature, upon defining a radiofrequency treatment, whilst patents that develop a methodology consisting in the injection of an sclerosant substance, such as WO2009100435 by RICHARD W. BOCK, which defines the intravenous injection of a sclerosant with a certain composition and patent JP20060216894 by JMS Co, which also defines a medical fluid connector that enables different fluids and gasses to be mixed in order to create a foam for the treatment of varicose veins, should also be acknowledged, although the latter does not have just one opening in its distal portion. Similarly, patent EP1377328 by PENTAFERTE SPA should be taken into consideration, since it defines a foam injection device designed to treat varicose veins, which resembles a syringe. Finally, patent EP2269578 by BTG INTERNATIONAL deserves background recognition, upon defining a device designed to introduce microfoams, which defines a tube diameter and the generation of said foam with characteristics specific to said device.

Patent EP2596759 by TECHLAMED SRL must also be highlighted, since it defines a method for treating varicose veins, whereby the varicose vein is firstly treated using a laser, before a sclerosant treatment is subsequently applied in the form of foam. Nevertheless, this patent differs from that of the present application in many different ways, for example, in that it does not permit the two treatments to be carried out synergistically, in synchronization and in that it refers to firstly introducing the laser through the catheter, emitting the energy, removing the laser and subsequently injecting the sclerosant substance once the laser has been removed, finally taking the catheter or tube out, thus demonstrating that it is by no means synchronized, in addition to requiring much greater power flows than those required by the invention object of the present patent, all the while using instruments known about on the market, without this instrumentation introducing any kind of novelty whatsoever. As will become evident throughout this description, not only will the present invention better and improve upon this instrumentation, but rather upon the methodology as well, given that the new patent gives rise to the simultaneous chemical and thermal removal of varicose veins, thus reinforcing the effects of both treatment aspects, making it possible to reduce energy concentration and the amount of medication administered, whilst increasing efficacy and making it possible to work without local anesthetic, be it tumescent, perivenous and/or truncal.

The use of the above techniques for treating truncal varicose veins, which, little by little, have become less invasive, constitutes a major advancement in the treatment of the same, in converting a purely surgical treatment into a less aggressive treatment, which can be carried out fully at outpatient centers. All of the above techniques seem to be effective when carried out by expert hands. Indeed, the results obtained using the endolaser technique have proven to be highly effective, despite requiring local anesthetic to be introduced in various different ways, including in a perivenous, tumescent and truncal manner, in order for this practice to be carried out, given that the energy released inside the vein, which comes into contact with the vascular endothelium, gives rise to heat removal, thus requiring analgesic-anesthetic in order to proceed correctly.

However, the new device object of the present invention has made it possible to develop a new method, by means of synthesizing two techniques, which does not require local anesthetic in order to successfully irritate the venous endothelium and consequently remove truncal varicose veins, it thereby being possible to practice this method during medical consultations using the pertinent asepsis measures, without the need for a strict surgical environment. There are no diameter limits for venous confluences or for the path thereof. In fact, it is possible to confirm immediate response one hundred percent reliably by means of echography. This immediate response is achieved by no more than 8 to 10 cc of sclerosant microfoam, at 1.5 to 2%, which is administered and controlled by means of echography, thus enabling us to complement treatment synergistically by means of the heat action of the laser, with a minimal energy dose, thereby eliminating the need to use anesthetic and making it possible to carry this technique out at outpatient clinics alone.

DESCRIPTION OF THE INVENTION

The present invention described herein is a device designed to treat varicose veins, which makes it possible to apply a new treatment method.

Optical fibers are often made up of one filament, which constitutes the optical fiber itself. Said optical fiber is covered or coated in a material, which in general, is joined to it. In the present invention, between the filament or optical fiber and the coating or outer casing, there is a large enough gap for a liquid, air, foam or other sclerosant substances to flow though. As such, a double-part conduct is mentioned throughout the specification and subsequent claims, this conduct housing an optical fiber with or without a common coating, facilitating the passage of said irritant and/or sealant sclerosant substances.

As such, the device consists of a double-part conduct, which houses an optical fiber and has a "T" connection, which facilitates the passages of substances or medication from a connection key to the conduct itself.

This conduct may be variable in diameter, so as to house the optical fiber that may have a diameter of between 50 and 1000 microns, and the rest of the space or channel, from the optical fiber to the coating or outer casing of the conduct, which facilitates the passage of the abovementioned substances, which may measure between approximately 0.5 and 3 mm. Said conduct facilitates the passage of energy though the optical fiber, releasing this energy in the desired area, facilitating the passage of medication via the double-part conduct and releasing it in the desired area. In the most common case, the optical fiber would be in the order of 400 microns, whilst the total conduct assembly would be in the order of 0.5 to 3 mm.

In order to ensure correct functioning, the transmission capacity of the laser energy would have a variable wavelength range, suited to said method, from 750 nm to any wavelength that may be used with said optical fiber, preferably measuring between 810 nm and 2100 nm.

The connection between the optical fiber and the laser apparatus may be universal or particular to each type of specific laser to be used in each specific case.

There is an end piece at the end of the conduct, which is made of metal and may be cylindrical, ovoid-shaped or rounded, in the shape of a ball or another shape, which is high-quality (plastic, quartz, silica, etc.), which adapts to the characteristics of the double-part conduct, having a central and/or side opening though which the laser beam exits.

As already mentioned, the conduct houses the optical fiber, which may be coated, and has a double-part conduct or channel that facilitates the passage of substances or medications, which may constitute a gas, liquid, vapor and sclerosant foam substances and/or sclerosant sealant substances for treating varicose veins. These products may constitute:

Sclerosant medication in liquid form, or in foam, microfoam or Foam form. Currently, the most frequently used include Polidocanol, Lauromacrogol 400, sodium tetradecyl sulfate, iodinated substances, glycerins or any other substances or medications capable of producing a venous endothelium reaction, which leads to irritation, removal, sealing and subsequent healing of the vein or varicose vein treated, the same being administered in either liquid or microfoam/foam form.

Sclerosant liquid medication, which, when mixed with other medications and/or gasses (air, $O_2$, $CO_2$, Helium, noble gasses or other) may produce a foaming effect capable of irritating the venous endothelium.

Liquid and/or microfoam medicines or substances capable of giving pigment, fixing and/or coloring the venous endothelium, which are also capable of better capturing the laser energy released inside the vein and/or varicose vein to be treated, using less energy or even the minimal amount of energy required to produce the required effect.

Liquid medications or substances with local anesthetic properties to act on the venous endothelium and/or mixed with sclerosant agents, like those mentioned above.

Substances that directly seal the venous endothelium, for example cyanoacrylates or others.

Liquid at a low temperature, in order to produce a venous vasospasm (cryotherapy), to be combined with the effect of the laser in order to successfully remove the vein in question.

Liquid or water vapor at high temperatures, in order to achieve heat removal by means of water vapor, which may be combined with the effect of the laser.

Or any other type of substance used to treat varicose veins.

It has a "T" connection, which facilitates the direct passage of the substances or medications specified above from a three-way key or female-female connection key to the inside of the double-part conduct. This connection is located at a distance of between 25 and 65 cm away from the end point or distal end of the conduct, so as to enable the substances or medication injected at the "T" connection to be transferred and act effectively, without deteriorating along their trajectory. A small valve or anti-return device may be added towards the portion close to the conduct, although the substances or medications tend to flow towards the distal opening naturally.

The conduct may be marked in millimeters and/or centimeters and has small openings at the distal end, in order to facilitate the passage of the substances or medication now in foam state, in such a way that they may pass from the inside of the double-part channel to the inside of the vein/varicose vein from the side and from the front or axially, via the front opening. These openings constitute small side holes or perforations in the outer face or casing of the conduct, located such that they are parallel to each side of the distal side portion. The number "n" of holes may vary, preferably being between 1 and 10, with 5 at each side constituting the optimal number. The distance separating these holes would be in the order of 0.15 to 0.55 mm. The distance from the last hole to the distal end of the conduct would be in the order of 0.4 to 1.1 cm. The diameter of these holes would be variable, at around 0.05 to 0.5 mm, bearing in mind that the smaller the diameter, the better, since, upon injecting the substance or medication, in addition to the pressure exerted on the "T" connection, more turbulence, and hence, more foam, is produced. In addition, the action surface of the substances or medication in the vein or varicose vein increases considerably.

The characteristics of the optical fiber material, as well as of the double-part conduct, are those often used in general, i.e. silica-silica, quartz or similar.

As such, the great innovation of this device is that it facilitates synergistic, independent or combined use of the properties of the heat energy provided by the laser and released inside the vein, with intimate contact with the venous endothelium or without specific contact, deriving benefit from the calorific and heat energy linked to the independent action, with the properties of the substances or medications introduced through the double-part channel or conduct.

Action may be synergistic and/or independent, synchronized or combined, in such a way that the chemical effect of the sclerosant substance injected in liquid and/or foam form produces a vasospasm and endothelial irritation, facilitating the thermal action of the laser upon the energy being freed inside the vein to be treated with the minimum amount of energy needed to prove effective, without the need to administer local anesthetic or, if required with the same. This facilitates the removal of the vein and/or varicose vein treated, thus resulting in obliteration, closure and sealing in the treated area. As such, the vein and/or varicose vein will disappear and the area where it was will heal.

The action may also be inversely synergistic, i.e., with heat energy from the laser, which is either in contact or not in contact with the venous endothelium, firstly being released, before or whilst the vascular endothelium sclerosant or irritant substance or medication is introduced. In either case, the energy density and/or the concentration of substances used reinforce one another synergistically to obtain the desired sealing, closure and subsequent healing result of the vein and/or truncal and or collateral varicose vein treated. This synergistic action facilitates both a reduction in energy and/or in energy density deposited inside the vein or varicose vein to be treated or in contact with the venous endothelium and also the reduction in the concentration of the sclerosant medication injected in liquid and/or foam form.

As such, the technique used to treat truncal varicose veins by means of this device, which may be referred to as a synergistic Endolaser use for Removal and Foams/foams or E.L.A.F, consists in:

1.—Introducing the conduct with the optical fiber into the varicose vein or truncal vein (or vein to be treated, which may be accessed through the optical fiber).

This introduction may be made by means of the Seldinger technique, with an introductory tool, guide, catheter or through the same, introducing the optical fiber into the vein, or by means of dissection, opening and introducing the fiber inside the vein directly, without the need for a catheter.

The whole process may be controlled by echography and other radiological means, if required. Local anesthetic is only required at the point of entry.

Echographs and echo-dopplers are now commonly used to visualize the position of the end of the optical fiber through the catheter or without the same, at approximately 2 cm away from the sapheno-femoral or sapheno-popliteal join—junction. In this case, they can also be used to see how the medication administered enters and to observe the effect produced inside the vein (venous spasm), in addition to observing the phenomena produced upon shooting the laser and releasing heat energy from the same inside the vein, and also in contact with the venous endothelium.

2.—Introducing substances inside the conduct along the channel or double-part conduct thereof by means of a "T" valve and three-way key, depositing them inside the vein through the same.

It is possible to introduce the types of substances or medication mentioned earlier.

They are introduced through a three-way key connected to a "T" shaped valve coupled thereto, or which forms the same body with the optical fiber and the double channel or double-part conduct, which is located at between 25 and 65 cm away from the distal end of the optical fiber. As such, the medication passes directly through the double-part conduct, therefore not losing foaming capacity, since the medications were prepared for such a short course, measuring from 25 to 65 cm, from the injection of the same to their passage inside the vein or varicose vein to be treated. The medication that passes into the distal portion thereof through small side openings in the double-part conduct designed to this end, as well as though the distal portion through a small central hole, through which the energy of the laser is also released inside the vein or varicose vein, either in direct contact with the vascular endothelium or inside the vein or varicose vein.

3. Physio-chemical synergy

The synergy of the action is produced in this case upon firstly introducing the sclerosant substance in the form of microfoam/foam, which gives rise to a venous spasm and endothelial irritation, whilst at the same time, heat energy from the laser is released through the optical fiber to the wall or inside of the vessel, whether or not in direct contact. The important aspect of this mechanism is that the vasospasm produced enables us to release the minimum amount of energy required to take effect, whilst removing the need for local anesthetic, thereby injuring, irritating, obliterating and removing the vein or varicose vein treated by means of heat, before sealing it, followed by subsequent healing.

As such, it is also possible to reduce the concentration of foaming sclerosant medication, such that, using concentrations of 1-1.5-2%, in quantities of no more than 10 cc, we can successfully introduce a venous spasm, whilst meanwhile irritating the venous endothelium, which is observed by means of echography. The usual mix would have to be 3-5 cc of sclerosant substance and 1.5-3 cc of air, in order to produce 8-10 cc of medication.

At the same time or two to three seconds later, the energy of the laser is released, the same having been reduced from 10-12 watts in the usual endolaser method, to 1.5-5 watts, according to the type of laser.

The continuous mode is generally used for three seconds at 1.5-5 watts millimeter to millimeter or for 3-4 seconds at 4 watts, in pulse mode (60 ms-100 ms), according to the type of laser.

As such, the synergic protocol constitutes:

Injecting the sclerosant material in the form of microfoam, at the mentioned concentration.

Immediately shooting the laser so as to release energy in the dosage and time interval set out, be it continuously or in pulses.

As such, the vein or varicose vein treated is closed, occluded and subsequently healed, without the need for local anesthetic (perivenous, tumescent and/or truncal).

This means the technique may be carried out fully at outpatient clinics, not requiring high doses of anesthetic at the access point, nor high doses of sclerosant substances and laser heat energy.

4. Protocol for removing the conduct and optical fiber.

The conduct and fiber must be flexible and it must be possible to sterilize them after use. Once the conduct has been introduced and has reached the point of application, the conduct or optical fiber, or the optical fiber alone, may be removed manually or using an automatic removal device, adapted to the optical fiber to this end.

As such, bearing the above point in mind, once the medication has been injected at concentrations of 0.2-0.5 cc and passes to the inside of the vein, it produces a vasospasm and irritates the venous endothelium.

Meanwhile, in synchronization, the laser is fired. It may be shot continuously for a period of 3-4 seconds at 1.5-5 Watts or in pulses from 60 ms to 100 ms for a period of 3-4 seconds at 4 Watts, according to the type of laser.

The above process is then restarted, causing a 1 to 2 mm retraction and the previous process is repeated. The entire cycle must be carried out along the entire trajectory of the vein to be treated, millimeter per millimeter. This process may be carried out manually or with the help of an automatic removal device, designed especially for this kind of conduct.

Finally, external help is also available by means of an external cold or cooling system, to be used as we fire the laser.

In order to complete the present description, with the aim of facilitating a better understanding of the characteristics of the invention, the same is accompanied by a set of drawings, which constitute an integral part thereof and facilitate a non-limiting illustration of the following:

FIG. 1.—Shows the device along the vein, wherein it is possible to observe the conduct that houses the optical fiber and its coating, and in turn, the channel through which medication passes, the "T" connection, the front opening and the side openings therein.

FIG. 2.—Shows the device once acting synergistically with the laser and the medication.

FIG. 3.—Shows the device being used on a patient.

DESCRIPTION OF THE DRAWINGS

As can be seen in FIGS. 1 and 3, along the length of the vein or varicose vein (1) to be treated, a double-part conduct (2) is introduced such that it reaches the area to be treated. The conduct (2), which houses an optical fiber (3), has a space or channel (4) through which the medication flows. Said conduct (2) has a "T" shaped connection (5).

The optical fiber (3) is responsible for shooting the laser (31) by releasing energy at the dosage and time intervals set out. This optical fiber may or may not be coated.

Figure 1:
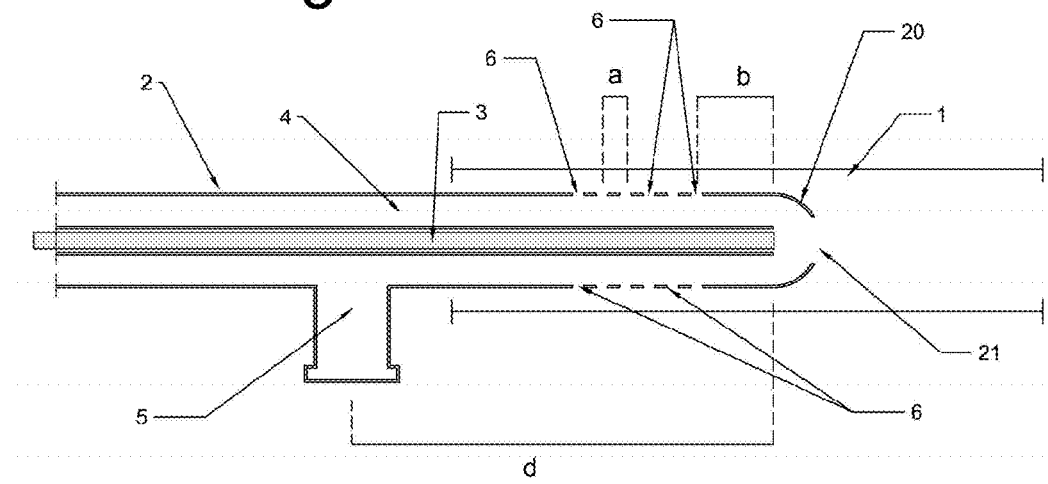

The double-part conduct (2) has a space between the optical fiber (3) and the outer coating (22) of the conduct (2), this space being referred to as a channel (4).

The "T" connection is responsible for preparing the mixture and introducing sclerosant substances and medication (51) into the conduct (2) through the double-part or channel (4) thereof.

The conduct (2) has a front opening (21), the shape and diameter of which may vary, thus facilitating the passage of the laser (31) and substances (41) or medication.

The "T" connection (5) is located at between 25 and 65 cm away from the distal end of the conduct (2) in length (d).

The diameter of the conduct (2) would be variable, generally measuring between 1 and 3 mm. This conduct (2) may be marked with centimeters and/or millimeters and has small openings (6) at its distal end, which facilitate the passage of the medication (51). These openings (6) constitute small side openings or perforations in the plastic outer face or coating (22) of the conduct (2), located such that they are parallel to each side of said outer covering (22). The number "n" of openings may be variable, preferably ranging between 1 and 10, with 5 on each side being the optimal number. The distance (a) separating these openings will be in the order of 0.15 to 0.55 mm. The distance (b) from the last opening or the opening closest to the distal end (20) of the conduct (2) and said distal end (20) will be in the order of 0.35 to 1.15 cm. The diameter of these openings (6) will be variable, in the order of 0.05 and 0.25 mm and the smaller, the better.

The range of wavelengths used to transmit the laser's (31) energy may vary from 750 nm to any wavelength that may be used with said optical fiber, preferably ranging between 810 nm and 2100 nm.

The "T" shaped connection (5) facilitates the direct passage of the substances (41) or medication from a three-way key (52) or female-female connection key, into the inside of the channel (4) of the double-part conduct.

Figure 2:
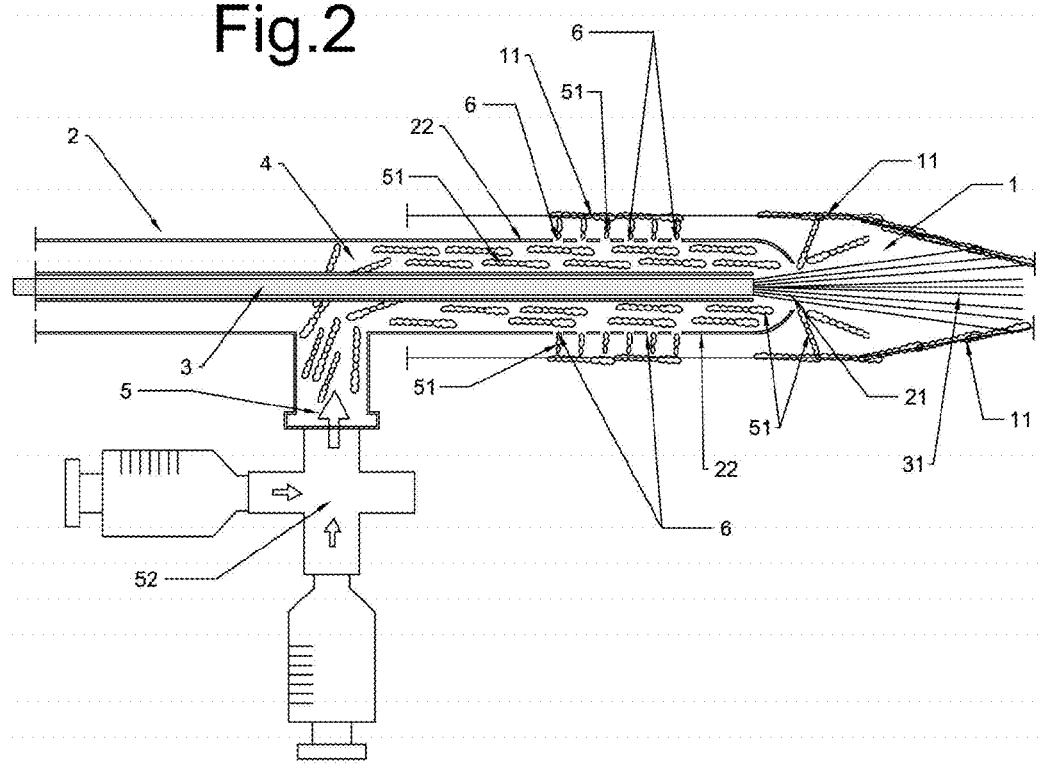

As can be seen in FIGS. 2 and 3, this device facilitates physio-chemical synergy between the action of the laser (31) and the action of the medication (51).

The front opening (21) facilitates the passage of the laser (31) and the sclerosant substances or medication (51) now in foam or microfoam form. In turn, the openings (6) facilitate the passage of the sclerosant substances or medication (51) in the sides of the vein (1) in foam or microfoam form, such that the action surface (11) increases considerably.

Finally, in FIG. 3, it is possible to observe the device being used on a patient.

Having described the nature of the invention in sufficient detail, bearing in mind that the terms employed in the present specification must be understood in their broadest, non-limiting sense, as is also the case of the description of the practical method for putting the device into practice, and having demonstrated that the same constitutes a positive technical advancement, we hereby seek to register the patent, i.e. to protect that which constitutes the essence of the invention referred to, which is captured in the claims below.

The invention claimed is:

1. A device for treating a truncal and/or collateral varicose vein, the device comprising:
   a conduct housing a coated optical fiber, wherein, at a distal end thereof, there is an opening, and wherein the shape of the distal end is variable;
   a channel constituting a space between the optical fiber and an outer coating along a length of the entire conduct, forming a double-part conduct;
   a T-shaped connection located at a distance that is between 25 and 65 cm away from the distal end, wherein a key that connects to the channel is coupled to said T-shaped connection;
   a number n of small holes located such that the small holes are parallel to each side of the outer coating, wherein the small holes facilitate an output of a medication in the form of a foam, where $1 \leq n \leq 10$.

2. The device according to claim 1, wherein there is a distance of between 0.4 cm and 1.1 cm between one hole of the small holes closest to the distal end of the conduct and said distal end.

3. The device according to claim 1, wherein the small holes are separated by a distance of between 0.15 mm and 0.55 mm.

4. The device according to claim 1, wherein the diameter of a hole of the small holes is between 0.05 mm and 0.5 mm.

5. A physio-chemical method using the device according to claim 1, the method comprising:
   a) introducing the conduct housing the optical fiber into an inside of the varicose vein until reaching an area to be acted upon, this process being controlled by means of echography;
   b) introducing components and said medication into a three-way key, mixing said components and introducing them via the T-shaped connection for said medication in the form of a foam, inside the channel of the conduct;
   c) injecting the medication by means of pressure, wherein the foam passes through the small holes and a front opening in the conduct, thereby giving rise to a venous spasm and irritating the venous endothelium, before immediately and/or synergistically firing a laser through the front opening to remove the varicose vein by means of heat and to subsequently seal the varicose vein; and
   d) removing between 1 and 2 mm of the conduct, and repeating step c), until treatment of the varicose vein is completed.

6. The physio-chemical method according to claim 5, wherein, in step b), a mixture of 3 cc to 5 cc of a sclerosant substance is prepared with 1.5 cc to 3 cc of air, in order to produce 8 cc to 10 cc of the medication.

7. The physio-chemical method according to claim 5, wherein, in step c), between 0.2 and 0.5 cc of the medication are injected, and the laser is fired continuously at between 1.5 and 5 Watts, for a time period of between 3 and 4 seconds.

8. The physio-chemical method according to claim 5, wherein, in step c), between 0.2 and 0.5 cc of the medication are injected, and the laser is fired in pulses of 60 ms to 100 ms for a time period of between 3 to 4 seconds at 4 Watts, the administration of the pulses depending on the type of laser.

* * * * *